United States Patent [19]
La Mori et al.

[11] 4,357,214
[45] Nov. 2, 1982

[54] USE OF GEOTHERMAL HEAT TO RECOVER ALCOHOL AND OTHER VALUABLE PRODUCTS

[75] Inventors: Phillip N. La Mori, Corona Del Mar; Raymond L. Zahradnik, Irvine, both of Calif.

[73] Assignee: Occidental Research Corporation, Irvine, Calif.

[21] Appl. No.: 119,669

[22] Filed: Feb. 8, 1980

[51] Int. Cl.³ .............................................. B01D 3/00
[52] U.S. Cl. .................................. 203/100; 60/641.5; 203/19; 203/88; 203/DIG. 13; 568/840; 568/913
[58] Field of Search ..................... 60/648, 641.2, 641.5; 165/45; 203/19, 100, DIG. 13, 88; 435/163, 165; 48/197 R; 568/840, 913

[56] References Cited

U.S. PATENT DOCUMENTS 3,470,943 10/1969 Van Huisen .......................... 165/45
3,858,397 1/1975 Jacoby ............................... 165/45 X
3,864,208 2/1975 Van Huisen .................... 60/641.2 X
4,078,904 3/1978 Galt et al. ........................ 48/197 R
4,085,795 4/1978 Gill ................................ 60/641.2 X Primary Examiner—Allen M. Ostrager
Assistant Examiner—Stephen F. Husar
Attorney, Agent, or Firm—Walter A. Hackler; Max Geldin

[57] ABSTRACT

Method for the use of heat, especially "Waste Heat", from geothermal steam or brines for the manufacture of chemicals such as alcohol, which comprises, according to one embodiment, flashing the brine to produce steam, passing the steam to a turbine for electrical energy generation, and employing the steam from the turbine discharge and/or the flashed brine to provide some or all of the heat requirements for the fermentation-distillation process for production of alcohols, e.g. (methanol and/or ethanol) from agricultural wastes. The method can also be utilized for the production by distillation and/or by industrial fermentation and/or by hydrolysis of other chemicals (such as furfural and acetone).

6 Claims, 6 Drawing Figures

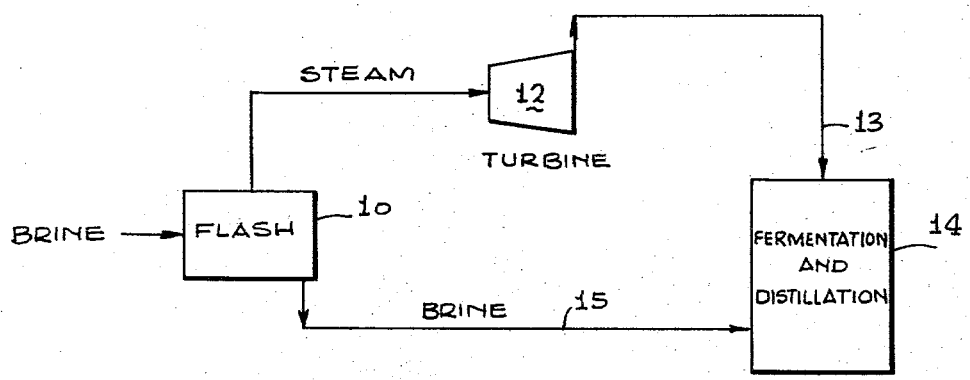
FIG. 1
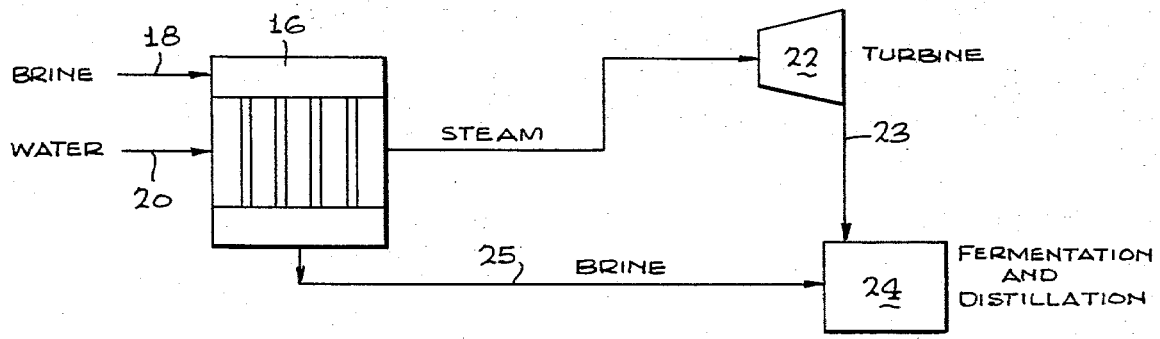
FIG. 2
FIG. 3
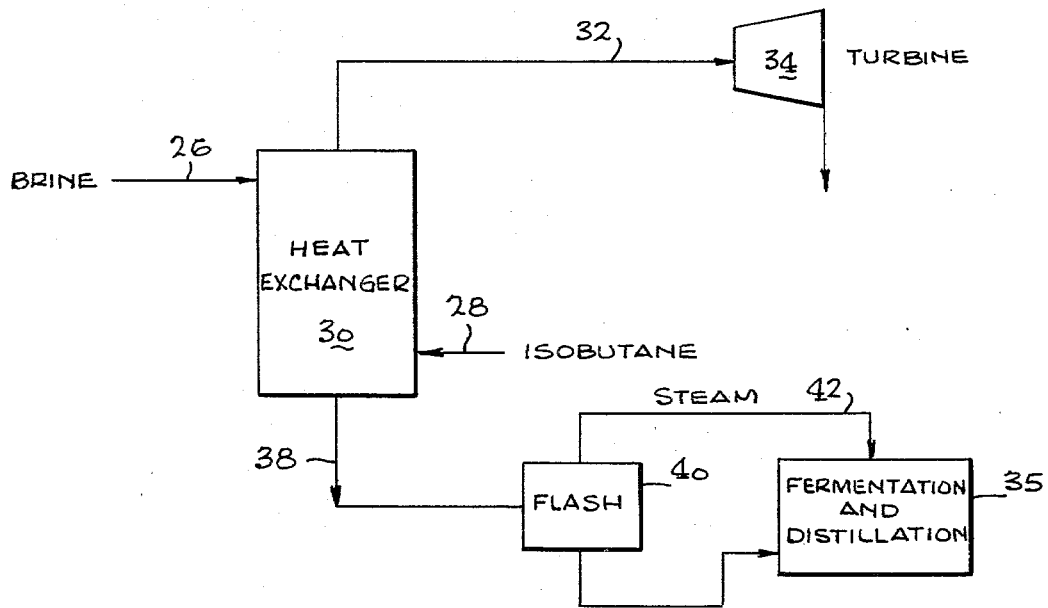

USE OF GEOTHERMAL HEAT TO RECOVER ALCOHOL AND OTHER VALUABLE PRODUCTS

BACKGROUND OF THE INVENTION

The present invention relates to the use of heat from geothermal fluids, including steam and brines, and is particularly concerned with the use of waste heat (i.e., heat contained in brine or steam which would normally be discarded, e.g., reinjected, as waste) from geothermal brine or steam obtained from geothermal energy power generation, for the manufacture of chemicals, particularly alcohol, by such processes as hydrolysis, fermentation and distillation. The geothermal source can be naturally occurring, or man made (as by atomic explosion underground and/or by injection of water or other heat exchange fluid into a deep well and/or by injection of a heat exchange fluid, e.g., water, into a spent shale retort).

Various methods are known for utilizing the geothermal steam or brine for electrical power generation. Thus, according to one procedure, the hot geothermal brine is directly flashed and the resulting flashed steam is then expanded through a turbine for electrical generation. According to another mode of procedure, a tube and shell heat exchange apparatus is employed for indirect heat exchange contact between the hot brine on one side and water or a working fluid on the other side, and the heated steam or working fluid is then passed to the turbine for generating power. Such methods are described for example, in *Geothermal Energy Utililization* by Edward F. Wahl, John Wiley & Sons, New York (1977).

According to a third method, direct contact heat exchange is provided between the geothermal brine and an immiscible (e.g., isobutane) working fluid, and the working fluid is expended through a turbine to produce electrical energy. Illustrations of the latter system are those disclosed in U.S. Pat. No. 3,988,895 to Sheinbaum, application Ser. No. 589,068, filed June 23, 1975 by S. F. Woinsky, application Ser. No. 873,264 of E. F. Wahl, et al, filed Jan. 30, 1978, and application Ser. No. 50,868, of P. Sadkukhan, filed June 21, 1979 (all of which are incorporated herein).

In all three of the above systems and processes, waste brine and/or steam (which still contains a substantial amount of heat) is obtained following electric power generation, and such waste brine or steam is usually at too low a temperature for economical energy conversion in large amounts.

It is well known to employ waste or exhaust steam from a power generating turbine for heating a distillation plant or evaporator. See, for example, U.S. Pat. Nos. 3,412,558; 3,243,359; and 3,451,220.

The object of the present invention is to utilize waste heat in the form of waste brine and/or exhaust steam from a power generating turbine powered by geothermal energy, in a novel manner for producing valuable chemicals. Thus, for example, substantially anhydrous liquid alcohols are high grade fuels or can be used as high grade fuels. Gasoline with about 10% ethanol is called gasohol. Fermentation of sugar or starch can be used to transform the sugar or starch to ethyl alcohol and carbon dioxide. Industrial alcohol can be made from agricultural wastes by first digesting the waste to sugars and fermenting the sugars to form dilute ethyl alcohol, then distilling the dilute alcohol to obtain concentrated alcohol, that is at least about 90%, typically 95% alcohol. However, heat is required for carrying out digestion (including enzymatic acid or base catalyzed hydrolysis, as hydrolysis of starch or cellulose), fermentation, and distillation operations.

SUMMARY OF THE INVENTION

According to the invention, the low quality energy from geothermal steam fluids or brines, e.g., use of brines and/or steam following electrical power generation or direct use of low enthalpy brines or steam, can conveniently and effectively be employed for the production of chemicals from source materials or organic residues, such as agricultural products, which can be readily fermented and/or hydrolyzed and/or distilled utilizing such low quality energy, particularly for production of alcohol, e.g., ethyl alcohol.

Ethyl alcohol can be derived by fermentation processes using any material in which the carbohydrate is present in the form of sugar or, as with starch, which can be converted to sugar.

There are three major types of agricultural raw materials which can be used, including sugar, starches, and cellulose materials. Sugars, as from sugar cane, sugar beets, molasses sweet sorghum, and fruit or fruit juices can be converted by fermentation to ethyl alcohol and carbon dioxide directly. Starches, such as from whey, grain and potatoes, must first be digested or hydrolyzed to fermentable sugars, as by the action of enzymes from malt or mold, followed by fermentation. Cellulose from wood, agricultural residues (e.g., bagasse), and the like, which do not contain sugars, must likewise be converted, in this case by the action of enzymes and/or mineral acids (hydrolysis) in order to produce both methanol and ethanol. Once simple sugars are formed, enzymes from yeast can readily ferment them to alcohols (especially ethyl alcohol). Typically, following fermentation of sugars, a 6 to 10% solution of alcohol is obtained which is then fractionally distilled, to produce about 90 to 95% alcohol. With wood or with agricultural wastes, such as corn and wheat straw, at least about three gallons of methanol are usually produced for every one gallon of ethanol; however, ethanol can be produced directly from cellulose with the correct enzymes.

The above processes for producing alcohols are known in the art (e.g., see Volume 8, *Encyclopedia of Chemical Technology*, Kirk-Othomer pp 871–880).

The majority of the geothermal heat for carrying out the fermentation or digestion-fermentation of alcohol, e.g., from waste agricultural products, and the heat for distillation of the resulting alcohol can be derived from waste heat, e.g., the gaseous and liquid effluents in a geothermal electrical power plant (or, for that matter, any power plant which has a liquid or gaseous effluent at sufficiently elevated temperature). However, the waste heat can be derived in various ways as mentioned above and described more fully below either directly or indirectly from the geothermal brine. According to one preferred mode of operation, the geothermal fluid is flashed in a steam separator and high pressure steam is passed to a turbine for electric power production. If desired, and if the brine is at sufficiently high temperature, the brine can be doubly flashed and in each case used for electrical power generation. The steam discharged from the turbine or turbines, and the spent brine can both be used to supply the high temperature needs as well as the low temperature needs for the digestion-fermentation and distillation operations.

It is, of course, necessary that the temperature of the waste steam and spent geothermal brine be sufficiently high to provide the above necessary heat requirements. The present invention can be especially useful in those regions where there is geothermal energy in close proximity to large scale agricultural production (especially, if agricultural waste is to be converted to liquid or gaseous fuels). Another advantage of the invention in these regions is that large scale agricultural production can consume large amounts of the fuels and other products produced by the invention.

In the United States, the major regions where there are geothermal sources close to where crops are grown and/or packaged are The Imperial Valley, California; Southwest Idaho and adjacent parts of Oregon; Southeast Idaho and adjacent parts of Utah; Northern California; Central Washington; West-Central Oregon; and, The San Luis Valley, Colorado.

Various ways, in addition to direct flashing of the geothermal brine to steam, can be used to provide the heat requirements for fermentation and distillation according to the invention. Thus, use of a tube and shell apparatus permits indirect heat exchange contact between the hot brine, and water or a working fluid such as isobutane, employing the heated steam or working fluid to operate a power turbine, and employing the waste steam as well as the spent brine for fermentation and distillation.

Also, direct contact between the geothermal brine and an immiscible working fluid, and utilization of the working fluid in a turbine to produce electrical energy, can provide spent brine which can be used for the fermentation or digestion-fermentation and distillation process.

In the direct contact heat exchange system, the spent brine which can be at a temperature which is too low for further power generation, can still be sufficiently high in temperature to be useful for distillation, e.g., of ethanol or methanol, and the process can be carried out, for example, by using a working fluid in which ethanol is soluble, and then contacting the working fluid with the fermentation mash, e.g., in an indirect method employing a tube and shell apparatus. If the working fluid does not inhibit hydrolysis or fermentation and is insoluble in the material to be fermented (or hydrolyzed) and distilled, the working fluid can be run directly into the mash. As used herein, "mash" includes both fermentation media and hydrolysis or digestor reaction mixtures.

Alternatively, the waste brine can be passed through a tube and shell system to the mash to carry out the hydrolysis or fermentation, followed by distillation of the alcohol.

Where the direct contact method is employed between the geothermal brine and a working fluid such as isobutane, this can be carried out according to the method described and disclosed in Woinsky Application Ser. No. 589,068, the method of the above U.S. Pat. No. 3,988,895 of Sheinbaum, or alternatively, by the process of Wahl, et al, Ser. No. 873,264, filed Jan. 30, 1978, or of Sadhukhan, Ser. No. 50,868, filed June 21, 1979, and which is a continuation of Ser. No. 861,907, filed Dec. 19, 1977 (all of which are hereby incorporated herein). In the latter two processes, the brine passing through the systems is gradually reduced in temperature until it is discharged, and the brine so reduced in temperature can be employed to provide waste heat for the invention process.

In each of the above processes for power generation, the temperature of the spent brine can be sufficiently high to carry out the fermentation, or digestion-fermentation, or distillation operations; however, in some cases, heat may need to be used in addition to that from the spent brine.

DETAILED DESCRIPTION OF PREFERRED EMBODIMENTS

The invention will be more clearly understood by the detailed description of the embodiments described below taken in connection with the accompanying drawings wherein:

FIGS. 1, 2, and 3 illustrate direct brine flash, tube and shell apparatus and direct contact heat exchange for electrical power generation from geothermal brine, with the liquid and gaseous effluents employed for fermentation and distillation of alcohol.

Figure 4:
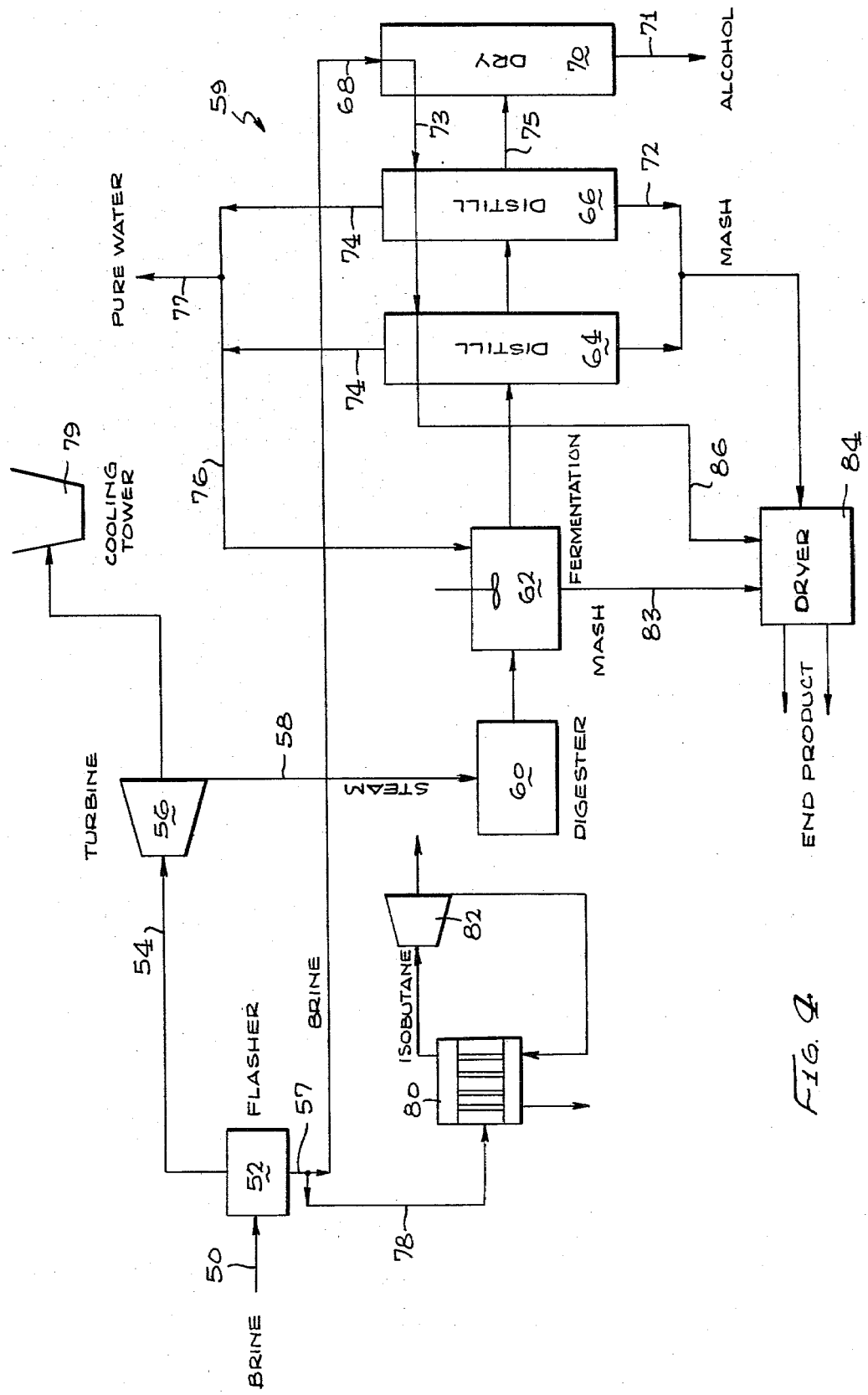
Figure 5:
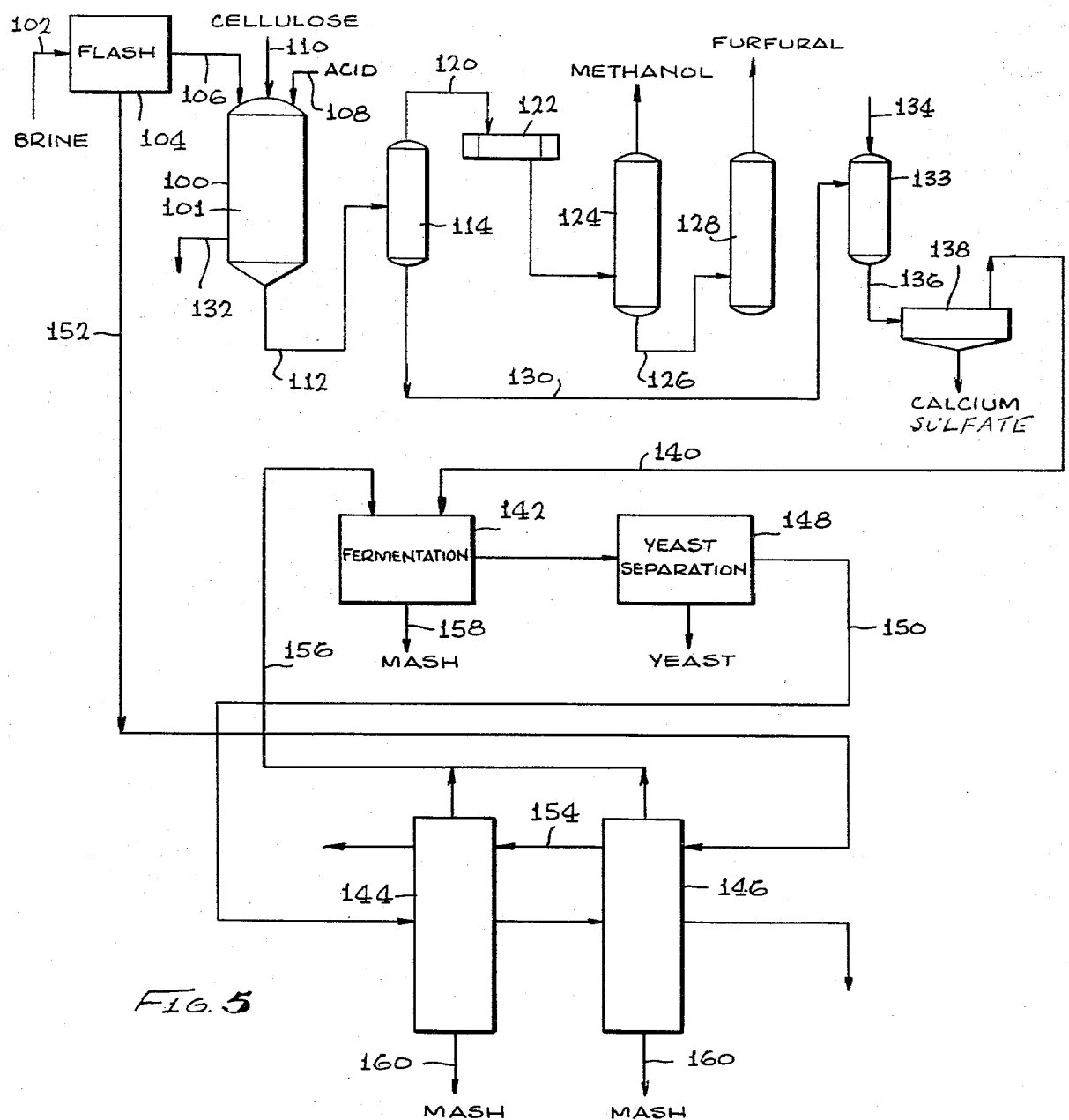
Figure 6:
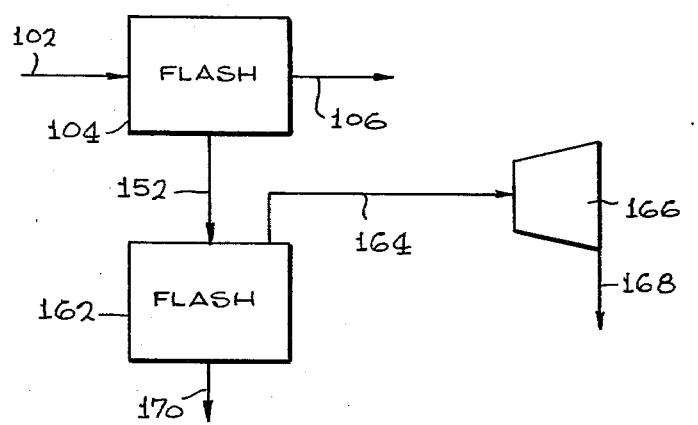

FIGS. 4, 5, and 6 illustrate more detailed, specific embodiments of the invention.

In FIG. 1, geothermal brine, e.g., at about 400° F., is flashed in the flasher and steam separator 10, and the steam generated is employed to power an electrical generating turbine 12. The discharged steam (at about 250° C. and 30 psia) 13 from the turbine and the discharged spent brine (about 325° F.) at 15 are fermentation and distillation operation indicated at 14 for producing alcohol, e.g., from fruit or fruit juices.

In FIG. 2, a tube and shell apparatus 16 is employed to provide indirect heat exchange contact between brine at 18 and water or a working fluid (e.g., isobutane) at 20, and the resulting steam or hot working fluid is used to power a turbine generator at 22, the exhaust steam at 23 and the spent brine at 25 being employed to supply the heat requirements for the fermentation-distillation operation at 24, e.g., for production of alcohol.

In FIG. 3, hot brine at 26 is brought into direct contact heat exchange with a working fluid such as isobutane at 28 in a heat exchanger 30, and the hot working fluid at 32 is passed to a power generating turbine 34 as described in Woinsky Ser. No. 589,068. In this modification, the spent brine at 38 still has sufficient heat so that when flashed at 40, the resulting steam at 42 can be employed in the fermentation-distillation operation, (e.g., 35, for production of alcohol).

FIG. 4 illustrates a specific embodiment and an example of a system for employing waste heat from geothermal brine used in power generation, for producing alcohol by digestion-fermentation and distillation according to the invention.

Referring to FIG. 4, geothermal brine at 50, and which can range in temperature from about 350° to about 600° F., e.g., 350° F., is introduced into a steam separator or flasher 52, and the flashed steam at 54 is introduced into a turbine 56 for generating electric power.

The steam discharge at 58 from the turbine 56 and also the spent brine at 57 from the steam separator or flasher 52 are then passed to an alcohol generating plant indicated generally at 59.

Some or all of the turbine discharge steam at 58, at 320° F., is then passed into a digestor 60 containing the raw feed stock, e.g., in the form of a mash such as grain containing a suitable enzyme such as malt. Under such high temperature conditions the feed stock at 60 is contacted for sufficient time to convert the mash substantially into a fermentable sugar. The converted starchy material at 60, now in the form of a sugar, is then transferred to a fermentation vessel 62.

In the fermentation vessel 62, the converted sugar is fermented, in the presence of an enzyme such as yeast, to ethyl alcohol by maintaining the temperature of fermentation at about 90° F. using hot water which is discharged from the alcohol distillation columns 64 and 66, as described hereinafter. The resulting mash in the fermentation vessel 62 contains a dilute, e.g., 6 to 10% solution, of alcohol. The dilute alcohol solution is removed from the fermentation vessel 62 and is introduced into distillation columns 64 and 66. Distillation of the alcohol occurs in both of the columns 64 and 66 by heat from the spent brine at 57 discharged from the steam separator or flasher 52 at a temperature of about 325° F. Such brine steam is first however, passed at 68 through a dryer 70 where the 95% alcohol product from column 66, is converted to 100 ethyl alcohol at temperature of about 150°-175° F. This is accomplished by adding to the dryer 70 a third component such as benzene, resulting in the dehydration of the alcohol to 100% alcohol which is recovered at 71. This dehydration is optional since for most fuel uses, the alcohol can contain as much as 30% water (but less than 10% water is preferred for internal combustion engine use). Alternate drying means are those, for example, on Page 13 of the Jan. 31, 1980 *Wall Street Journal* article by Meg Cox. The resulting brine stream at 73 is then passed into the distillation columns 66 and 64 in heat exchange relation with the dilute alcohol therein. This maintains proper temperature conditions of between about 150° and about 220° F. in such columns for the distillation of the dilute alcohol from the mash, which is withdrawn from columns 64 and 66, at 72. The about 95% alcohol produced in distillation columns 64 and 66 is transferred at 75 into the dryer 70.

Hot water and steam at about 206°-217° F. is withdrawn from distillation column 66, and hot water at temperature of about 103°-154° F. is withdrawn from the distillation column 64, and such hot water and/or steam can be combined at 76, and the combined steam introduced into the fermentation vessel 62 as noted above. A substantial amount of pure water at 77 can also be obtained for water supply or for cooling tower use at 79. A portion of the brine from the steam separator can be passed at 78 into a tube and shell heat exchanger 80 for heat exchange with a working fluid such as isobutane, and the heated isobutane can then be passed to a mechanical turbine 82 and the working fluid exhaust returned to the heat exchanger 80 to form a binary loop.

The mash at 83 withdrawn from the fermenter 62 is then pressed to remove water and the resulting mash dried in a dryer at 84 to provide a feed stock for heating or power production by burning, or as an animal food. The drying in dryer 84 can be carried out with exhaust brine at 86 from the distillation columns 64 and 66.

Thus the exhaust brine from direct or indirect contact heat exchange or from the steam separation is generally employed for the low temperature use of the alcohol plant and the exhaust steam from the power turbine generally is used for the higher temperature requirements. Such higher temperature requirements are generally for the conversion of the mash in the digestor 60, e.g., a mixture of water and ground corn, which generally requires a temperature of from about 320° to about 340° F.

According to a modification of the above process, the mash at 60 can be preheated with hot brine say to 300° F., and waste steam from the steam turbine as at 56 can be used to further heat the mash to the digestion temperature of say about 320° F., and then the spent brine and steam from the mash digestion chamber 60 can be combined to provide the necessary heat requirements for the remainder of the process including the distillation and drying steps.

The alcohol fermentation plant 59 is illustrative of known industrial plants, and is not, per se, novel.

Another alternative is to produce furfural, methanol and ethyl alcohol from cellulose or wood waste material. In the process shown in FIG. 5, wood waste or cellulose at 110 and sulfuric acid at 108 are charged to the digestor or hydrolyzer 100. For this purpose, a dilute hydrolysis solution from a previous batch can be pumped to the hydrolyzer or digestor 100, containing wood waste and sulfuric acid. Hot geothermal liquid brine at 102 and at a temperature of 400° F. or higher is flashed at 104, and the flashed steam at 106 is charged to the hydrolyzer 100, together with additional sulfuric acid, to raise the temperature in the hydrolyzer to a final temperature of about 385° F., equivalent to a vessel pressure of about 200 psig.

After a period of time, strong hydrolysis solution starts to flow out of the bottom of the hydrolyzer or digestor at 112 and is charged to a flash tank at 114. If desired, two of such flash stages can be employed, the first stage operating at about 50 psig and the second stage at atmospheric pressure. The flash vapor at 120 is condensed in a condenser 122 and the condensate containing both furfural and methanol is passed to a first distillation tower 124 for recovery of methanol, and from the base of tower 124, the bottoms at 126 is passed to a second distillation tower 128 for recovery of a furfural-water azeotrope.

The underflow from the flash stage or flash stages, at 114, is the sugar-containing solution at 130. At the end of the percolation cycle in digester 100, the lignin-rich residue at 132 can be recovered and used as a fuel.

The hot acid hydrolyzate solution at 130 is neutralized at 133 with a lime slurry at 134, and the resulting solution at 136 is fed to a sludge clarifier 138 for removal of calcium sulfate sludge.

The neutralized liquor at 140 is blended with recovered yeast from previous fermentation and passed to a fermentation tank at 142. Here, fermentation for conversion of the sugar to ethyl alcohol is carried out, using hot water which is discharged from the alcohol distillation columns 144 and 146. From the fermenters the fermented liquor passes to a yeast separator 148 for recovery of the yeast for recycle.

The dilute alcohol solution recovered at 150 is then introduced into distillation columns 144 and 146, as in the system shown in FIG. 4, for recovery of an about 95% alcohol product, by passage of the spent brine at 152 from the flash device 104 in heat exchange relation through the distillation columns, as indicated at 154, similar to the process of FIG. 4. If desired, dehydration of the 95% alcohol can be carried out as in FIG. 4, and described above, to produce about 100% alcohol, employing a dehydrating agent such as benzene, and spent brine for carrying out the dehydration or distillation in a drying or dehydration section.

Hot water and steam, as described in FIG. 4 above, withdrawn from the distillation columns at 156, can be introduced into the fermentation vessel 142 for maintaining the proper temperature therein for fermentation, as described above in the process of FIG. 4.

The mash withdrawn at 158 from the fermentation vessel 142 and from the distillation section as at 160 can be dried, as in FIG. 4.

A plant of the above type can achieve a conversion rate of about 50 gallons of ethanol per oven-dried ton of wood wastes.

A modification of the process of FIG. 5 is shown in FIG. 6. In this modification the liquid brine at 400° F. is flashed to produce steam at 106 for heating the hydrolysis mixture in digestor 100.

The brine discharge at 152 from flasher 104 can be again flashed in flasher 162 to produce steam at 325° F., and such steam fed to a work expander or turbine 166 to generate electrical power. The low pressure steam discharge at 168 from the turbine 166 can be used to preheat the hydrolysis solution fed to digester 100, or for other low quality heat uses. The brine discharged at 170 from the flasher 162 can then be used for heating and driving the alcohol distillation columns 144 and 146.

Another alternative is to produce ethanol (and other by-products, such as dried animal food) from sugar beets using heat from "spent" geothermal brine. For example, using a waste brine at about 275° F., beets of about 18% sugar content can be converted to fuel grade alcohol.

Briefly, in a process of the above type for conversion of sugar beets to ethanol, sugar beet stock, after cleaning and slicing, is fed to a sugar diffuser in which the sugar beet stock is steeped in water which is heated by passage of waste geothermal brine at 230° F. in heat exchange relation with the sugar diffuser, to produce a maximum temperature of 140° F. The resulting pulp is removed and dried for use as a cattle feed.

The sugar solution produced in the extraction process is then converted to ethanol in the fermenter, promoted by yeast. The temperature of the fermenter is maintained at about 90° F., and such temperature can be achieved by use of the waste geothermal brine from the diffuser at about 190° F.

The fermented mash is preheated to about 180° F. and is passed to a mash column which is heated by geothermal brine at about 270° F., and the dilute solution of alcohol and water withdrawn from the mash column is fed to a rectifying column. Spent brine from the mash column, at about 230° F. is used to heat the diffuser. In the rectifying column the about 8% alcohol solution leaving the fermenter is concentrated to about 95%.

The 95% alcohol solution is fed to a dehydration section comprised of a series of distillation columns, in the first of which benzene is introduced as a dehydration agent. Another portion of waste geothermal brine withdrawn from heating the mash column, at 230° F. is used to operate such distillation column, and the geothermal brine discharge from the sugar diffuser at 190° F. is used to heat another of the distillation columns in the dehydration section. A substantially 100% ethyl alcohol product can be obtained.

In the above process a sugar beet feed rate of about 168,000 pounds per hour is necessary for a 50,000 gallon-per-day ethanol unit, based on 18% sugar in the beets and extraction of 98.2% of the sugar.

Since the high temperature needs, according to one embodiment of the process, are supplied by removing steam from the back end of the turbine, thereby unloading the turbine back, this allows the front or high pressure stages of the turbine to be used more efficiently, e.g., to an efficiency up to about 80%. The net result is more efficient generation of electric energy and greater use of the geothermal fluid. The result is to produce alcohol with relatively little new energy input and permits recovery of additional products, e.g., chemicals and dry mash, for animal feed or fuel for electric power production, as well as the production of pure water up to 10 times the volume of the alcohol production. Due to the increased efficiency of the turbine, the heat rejection requirements of the electric power plant and water consumption are significantly reduced. The process can employ agricultural wastes as starting material and would result in significant improvements in the environment if agricultural wastes are fermented according to the present process, rather than burned. The term "agricultural waste" as used herein includes waste from forest products (e.g., wood chips, bark, sawdust, lignins and waste pulping liquids like sulfate liquor). The production of any $C_1$ to $C_5$ alcohol according to the present process can be used for producing gasahol by blending with gasoline.

It will be seen from the above that various modifications of the invention can be carried out. Thus, while the description above of the exemplary process is for the flash steam power cycle, the present process can be employed equally in binary cycle steam or even by employing the hot geothermal brine without power generation. In the case of the binary cycle, the high temperature needs of the fermentation-distillation process can be provided by using geothermal fluid from the well to produce steam in a heat exchanger before joining the regular cycle through the distillation column.

As previously noted, the present process is applicable for the production of various chemicals by hydrolysis and/or fermentation and/or distillation of suitable starting materials which can be hydrolyzed, fermented or distilled by use of the heat (especially waste heat) from geothermal brine. These include, e.g., the production of methanol, ethanol, isopropanol, 1-butanol, acetone, acetic acid, and where very high temperature brines up to 600° F. are available, the fermentation and distillation of materials requiring higher temperatures for fermentation and/or distillation can be employed, e.g., propanols, butanols, lactic acid, oxalic acid, citric acid, gallic acid, gluconic acid, and amino acids such as glutamic acid, as well as pharmaceuticals such as antibiotics and vitamins. See, for example, *Organic Chemistry*, Fieser and Fieser, D. C. Heath & Co., Boston 1950, pages 483–503, and the Kirth-Othmer reference, supra.

From the foregoing, it is seen that the invention can provide a simple, economical procedure for use of geothermal heat to recover various chemicals, e.g., alcohol, particularly from waste products, substantially without requiring the use of any additional heat or energy, except that in a geothermal brine (and/or steam).

It is to be understood that various changes and modifications of the present invention can be made in the spirit of the invention, and that the invention may be practiced otherwise than as specifically described, within the scope of the appended claims.

In commonly owned application Ser. No. 960,085, filed Nov. 13, 1978, of I-Kuen Yen (the entire disclosure which is incorporated herein) geothermal brine is used in si tu (i.e., within a hot geothermal zone) for chemical conversion. In contrast, in the present invention, the chemical conversion is done after the steam or brine leaves the well-head (or zone).

What is claimed is:

1. A process for producing ethanol from wood waste which comprises:
   (a) passing hot geothermal brine to a flash zone to flash off steam,
   (b) passing said flashed steam to a digestor containing wood waste and an acid for hydrolyzing said wood waste and forming a dilute solution comprising water, a fermentable sugar, furfural and methanol,
   (c) heating said dilute solution under conditions to convert said fermentable sugar to a dilute solution of ethanol contained in a mash, and
   (d) distilling said dilute solution of ethanol.

2. A process for producing an alcohol from organic matter which comprises:
   (a) passing hot geothermal brine to a flash zone to flash off steam,
   (b) passing said flashed steam to a digestor containing organic matter and an acid for hydrolyzing said organic matter and forming a dilute solution comprising a fermentable sugar,
   (c) heating said dilute solution under conditions to convert said fermentable sugar to alcohol, thereby forming a dilute solution of alcohol, and
   (d) distilling said dilute solution of alcohol.

3. A process for producing ethanol from wood waste which comprises:
   (a) passing hot geothermal brine to a flash zone to flash off steam,
   (b) passing said flashed steam to a digestor containing wood waste and an acid for hydrolyzing said wood waste and forming a dilute solution comprising water, a fermentable sugar, furfural and methanol,
   (c) flashing said solution to flash off vapors of furfural and methanol and produce a fermentable sugar solution,
   (d) heating said fermentable sugar solution under conditions to convert said sugar to a mash containing a dilute solution of ethanol, and,
   (e) distilling said dilute solution of ethanol.

4. A process for producing ethanol from wood waste which comprises:
   (a) passing hot geothermal brine to a flash zone to flash off steam,
   (b) passing said flashed steam to a digestor containing wood waste and an acid for hydrolyzing said wood waste and forming a dilute solution comprising water, a fermentable sugar, furfural and methanol,
   (c) flashing said solution to flash off vapors of furfural and methanol and produce a fermentable sugar solution,
   (d) heating said fermentable sugar solution under conditions to convert said sugar to ethanol contained in a dilute solution of ethanol contained in a mash,
   (e) transferring said mash containing said dilute solution of ethanol to a distillation zone,
   (f) discharging spent brine from said brine flash zone, and,
   (g) passing said brine discharged from said brine flash zone into said distillation zone in heat exchange relation with said dilute ethanol solution to distill said solution and produce a distillate comprising about 95% ethanol.

5. A process for producing ethanol from wood waste which comprises:
   (a) passing hot geothermal brine to a flash zone to flash off steam,
   (b) passing said flashed steam to a digestor containing wood waste and an acid for hydrolyzing said wood waste and forming a dilute solution comprising water, a fermentable sugar, furfural and methanol,
   (c) flashing said solution to flash off vapors of furfural and methanol and produce a fermentable sugar solution,
   (d) recovering said flashed off furfural and methanol,
   (e) treating said fermentable sugar solution with a calcium-containing base and removing the resulting calcium-containing sludge,
   (f) heating said lime-treated fermentable sugar solution under conditions to convert said sugar to a mash containing a dilute solution of ethanol,
   (g) transferring said mash containing said dilute solution of ethanol to a distillation zone,
   (h) discharging spent brine from said brine flash zone, and
   (i) passing said brine discharged from said brine flash zone into said distillation zone in heat exchange relation with said dilute ethanol solution to distill said solution and produce a distillate comprising about 95% ethanol.

6. The process as defined in claim 5, including adding benzene as dehydration agent to said distillate comprising about 95% alcohol, in a dehydration section, and introducing spent brine discharged from said brine flash zone in step (h) in heat exchange relation with said dehydration section, to dehydrate said distillate to produce about 100% alcohol, and then passing the resulting heat depleted brine from the dehydration section to said distillation zone.

* * * * *